(12) United States Patent
Yu

(10) Patent No.: US 12,329,687 B1
(45) Date of Patent: Jun. 17, 2025

(54) EYE MASK

(71) Applicant: SHENZHEN PUKAIYU TECHNOLOGY CO., LTD., Guangdong (CN)

(72) Inventor: Yonghua Yu, Guangdong (CN)

(73) Assignee: SHENZHEN PUKAIYU TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 18/935,697

(22) Filed: Nov. 4, 2024

(30) Foreign Application Priority Data

Sep. 12, 2024 (CN) .......................... 202422241732.1

(51) Int. Cl.
*A61F 9/04* (2006.01)

(52) U.S. Cl.
CPC ..................................... *A61F 9/04* (2013.01)

(58) Field of Classification Search
CPC ........................................................ A61F 9/04
See application file for complete search history.

(56) References Cited

U.S. PATENT DOCUMENTS

| 2009/0255026 | A1* | 10/2009 | Benner | ...................... | A61F 9/04 2/12 |
| 2020/0121004 | A1* | 4/2020 | Loughran | .............. | A62B 18/08 |
| 2023/0000188 | A1* | 1/2023 | Dubois | ...................... | A61F 9/04 |
| 2024/0115424 | A1* | 4/2024 | Oliver | ........................ | A61F 9/04 |

FOREIGN PATENT DOCUMENTS

CN     204931976 U   *   1/2016

OTHER PUBLICATIONS

Espacenet Translation of CN-204931976-U (Year: 2025).*
Ecosa, Foam Density and Quality Explained, May 4, 2023, https://www.ecosa.com.au/blog/post/memory-foam-density-and-quality.html (Year: 2023).*

* cited by examiner

*Primary Examiner* — Michael Zhang (57) ABSTRACT

An eye mask is provided in the present disclosure. The eye mask includes a first wrapping layer, a first flexible rebound layer, and a flexible support layer. The first wrapping layer includes an inner sheet and an outer sheet. A first accommodating cavity is defined between the inner sheet and the outer sheet. The first flexible rebound layer is received in the first accommodating cavity and attached to the inner sheet. The flexible support layer is received in the first accommodating cavity, attached to the first flexible rebound layer, and connected to the outer sheet. A rebound speed of the flexible support layer is faster than a rebound speed of the first flexible rebound layer.

18 Claims, 10 Drawing Sheets

EYE MASK

CROSS-REFERENCE TO RELATED APPLICATIONS

The present application claims the priority of the Chinese patent application No. 202422241732.1, filed on Sep. 12, 2024, and contents of which are incorporated herein by its entireties.

FIELD

The present disclosure relates to the field of articles for daily lives, and particularly to an eye mask.

BACKGROUND

An eye mask is commonly used to facilitate a user to fall asleep. In the art, high-resilience sponge may be filled to an interior of the eye mask. When users are wearing the eye mask for a long period of time, the high-resilience sponge exerts pressures on a peripheral area of the eyes, causing a discomfort sensation.

SUMMARY

An eye mask is provided in the present disclosure. The eye mask includes a first wrapping layer, a first flexible rebound layer, and a flexible support layer. The first wrapping layer includes an inner sheet and an outer sheet. A first accommodating cavity is defined between the inner sheet and the outer sheet. The first flexible rebound layer has a slow-rebound property. The first flexible rebound layer has a first rebound speed and is received in the first accommodating cavity and attached to the inner sheet. The flexible support layer is received in the first accommodating cavity, attached to the first flexible rebound layer, and connected to the outer sheet. A rebound speed of the flexible support layer is faster than a rebound speed of the first flexible rebound layer.

BRIEF DESCRIPTION OF THE DRAWINGS

To provide a clearer illustration of the technical solutions in the embodiments of the present disclosure or in the prior art, a brief introduction will be given to the drawings used in the description of the embodiments or the prior art. It is obvious that the drawings described below are merely some embodiments of the present disclosure, and for those skilled in the art, other drawings can be obtained based on these drawings without creative efforts.

REFERENCE NUMERALS IN THE DRAWINGS

1, first wrapping layer; 11, inner sheet; 12, outer sheet; 101, first accommodating cavity;
2, first flexible rebound layer;
3, flexible support layer; 31, shape-retaining portion; 32, support portion; 311, pre-connecting layer; 312, thickness layer; 3101, connecting side; 3121, second flexible rebound layer; 3122, flexible filling layer;
4, hemming member;
5, flexible nose support; 51, second wrapping layer; 52, third flexible rebound layer; 5101, second accommodating cavity;
6, strap; 61, third wrapping layer; 62, flexible connecting layer; 6101, third accommodating cavity.

DETAILED DESCRIPTION

Unless otherwise defined, all technical and scientific terms used herein have the same meaning as commonly understood by those skilled in the art to which this disclosure belongs. The terms used in the description of the application herein are intended for describing particular embodiments only and are not intended to limit the present disclosure. In the description, claims, and the above drawings of the present disclosure, the terms "comprising" and "having", as well as their variants, are intended to convey a non-exclusive inclusion. The terms "first", "second", etc., as used herein, are intended to distinguish between different objects, rather than to describe a particular order.

Reference to "embodiments" herein implies that a particular feature, structure, or characteristic described in connection with an embodiment may be included in at least one embodiment of the present disclosure. The appearance of the phrase at various places in the specification does not necessarily refer to the same embodiment, nor is it a separate or alternative embodiment that is mutually exclusive of other embodiments. One skilled in the art would explicitly and implicitly understand that the embodiments described herein can be combined with other embodiments.

In order to enable those skilled in the art to better understand the technical solutions of the present disclosure, the technical solutions in the embodiments of the present disclosure will be clearly and completely described below with reference to the accompanying drawings.

Referring to FIGS. 1-5, an eye mask is provided in an embodiment I of the present disclosure. The eye mask includes a first wrapping layer 1, a first flexible rebound layer 2, a flexible support layer 3, and a hemming member 4.

The first wrapping layer 1 includes an inner sheet 11 and an outer sheet 12. A first accommodating cavity 101 is defined between the inner sheet 11 and the outer sheet 12. Each of the inner sheet 11 and the outer sheet 12 is made of a fabric material. Specifically, the inner sheet 11 is made of a skin-friendly fabric material, such as nylon, and the outer sheet 12 is made of an air-permeable fabric material, such as cotton fiber. The hemming member 4 is arranged along an edge of the first wrapping layer 1 and is sewn to connect the inner sheet 11 to the outer sheet 12, thereby closing the first accommodating cavity 101.

Figure 2:
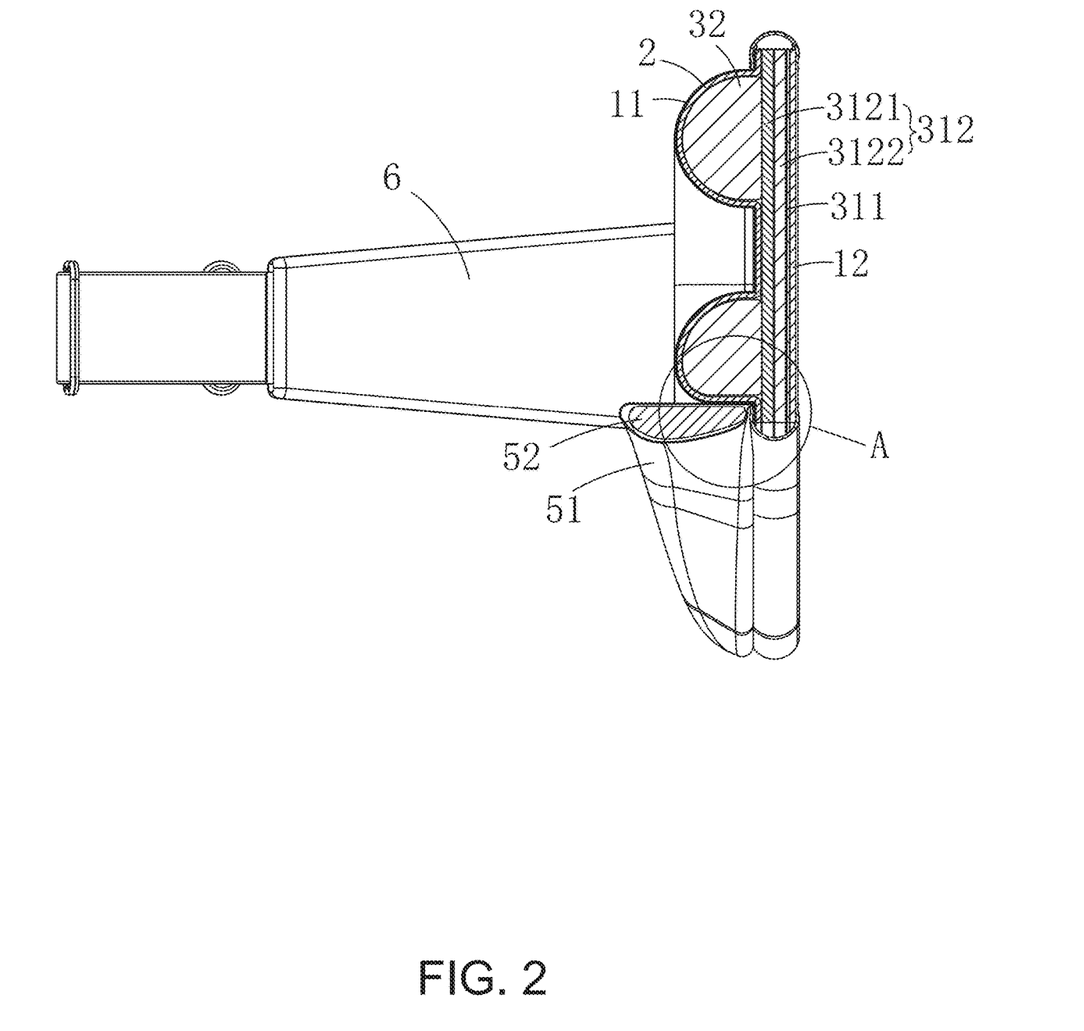
FIG. 2 is a sectional view of the eye mask of the Embodiment I.
Figure 3:
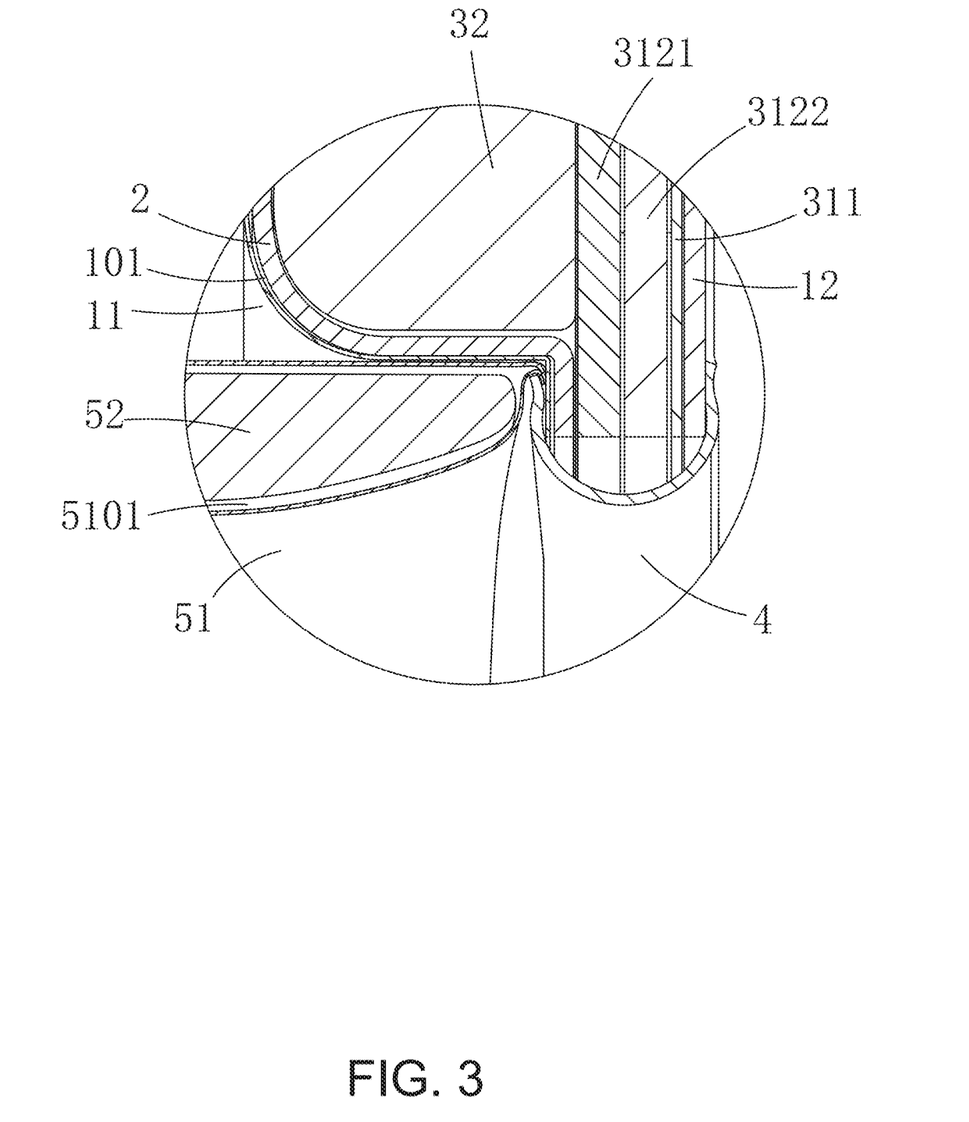
FIG. 3 is an enlarged view of a portion A in FIG. 2.
Figure 4:
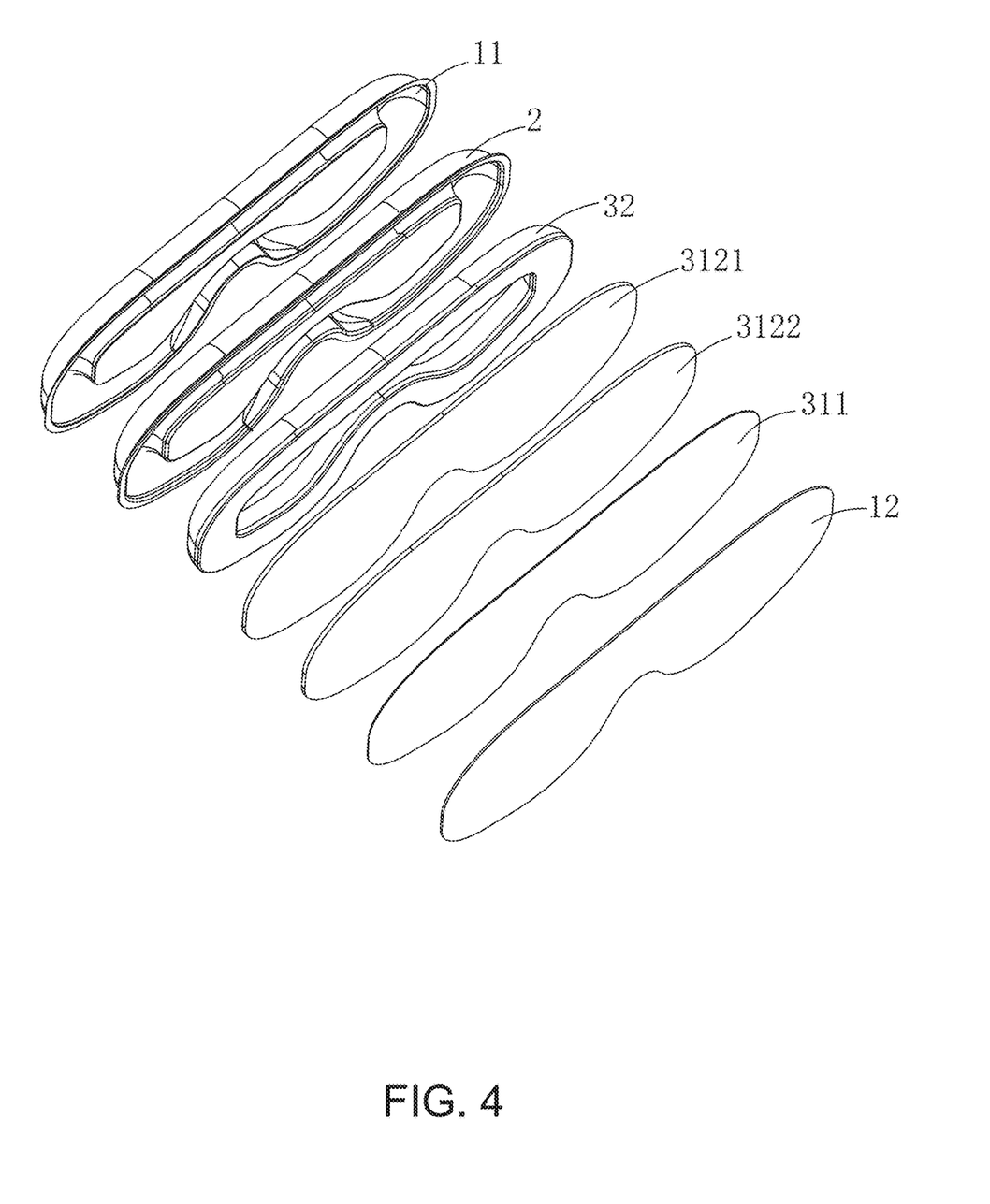
FIG. 4 is an exploded view of a partial structure of the eye mask in the Embodiment I.

The first flexible rebound layer 2 has a slow-rebound property, having a first rebound speed. The first flexible rebound layer 2 is received in the first accommodating cavity 101 and is attached to the inner sheet 11. Specifically, the first flexible rebound layer 2 is made of a slow-rebound sponge material (such as the memory foam or sponge). The slow-rebound sponge refers to a polyether-type polyurethane foam sponge that exhibits a slow-rebound mechanical property. The first flexible rebound layer 2 is bonded to the inner sheet 11 by an adhesive. A thickness of the first flexible rebound layer 2 is in a range of 0.5 mm-3 mm, for example, the thickness may be 1 mm.

The flexible support layer 3 is received in the first accommodating cavity 101 and is attached to the first flexible rebound layer 2. The flexible support layer 3 is connected to the outer sheet 12. A rebound speed of the flexible support layer 3 is faster than that of the first flexible rebound layer 2. That is, elasticity of the flexible support layer 3 is greater than that of the first flexible rebound layer 2. An elastic force provided by the flexible support layer 3 is substantially used to enable the eye mask to be reliably connected to the face of the user. To be noted that, when no external force is applied to the flexible support layer 3, the flexible support layer 3 is in its original state. When an external force is applied to the flexible support layer 3, the flexible support layer 3 is deformed and is in a compressed state. When the external force is eliminated, the flexible support layer 3, due to having flexibility, can be reset or recovered to its original state. The rebound speed refers to a speed of the flexible support layer 3 being reset or recovered from the compressed state to the original state.

The thinner first flexible rebound layer 2 may be firstly adhesively bonded to the inner sheet 11, enable the inner sheet 11 to be more resistant against folding and enabling a shape of the inner sheet 11 to be better maintained. Similarly, the flexible support layer 3 may also be adhesively bonded to the outer sheet 12.

The flexible support layer 3 includes a shape-retaining portion 31 and a support portion 32. The shape-retaining portion 31 has a connecting side 3101 facing the inner sheet 11. The support portion 32 is arranged in a strip shape or in a ring shape on the connecting side 3101. The shape-retaining portion 31, serving as a main functional body of the eye mask, is configured to shield eyes of the user from light. The support portion 32 is configured to contact the skin around the eyes, preventing the shape-retaining portion 31 from directly exerting pressures on the eyes, such that the user may wear the eye mask more comfortably. The support portion 32 has a thickness in a range of 6 mm to 15 mm, such as 10 mm, so as to accommodate a protruding shape of eyeballs. The first flexible rebound layer 2 is attached to the connecting side 3101 and covers the support portion 32, ensuring the skin-friendly material to contact the skin of the user, providing a smooth and comfortable touch.

The first flexible rebound layer 2 is slowly reset from deformation, and that is, the side of the eye mask that contacts the face of the user has less elasticity. In this way, the pressure applied on the facial skin is reduced, and the user may wear the eye mask more comfortably. The highly elastic flexible support layer 3 enables the eye mask to reliably contact the face of the user, such that the eye mask is prevented from sliding or falling off from the face.

Furthermore, in the present embodiment, the support portion 32 is in a shape of a ring. The support portion 32 is arranged as a closed loop, surrounding the edge of the shape-retaining portion 31, and the two eyes of the user are encircled by the one closed-loop support portion 32.

As shown in FIGS. 2-4, in the present embodiment, in order to facilitate production and shaping of the sponge, the support portion 32 and the shape-retaining portion 31 are prepared separately, and materials for preparing the support portion 32 and the shape-retaining portion 31 are not entirely the same to each other. A rebound speed of the support portion 32 is faster than that of the first flexible rebound layer 2. A rebound speed of at least a portion of the shape-retaining portion 31 is slower than that of the support portion 32. Specifically, the support portion 32 is made of a conventional sponge material, more particularly, a polyurethane foam sponge material. A rebound speed of the support portion 32 is faster than that of the first flexible rebound layer 2. The shape-retaining portion 31 includes a pre-connecting layer 311 and a thickness layer 312. The pre-connecting layer 311 is made of the conventional sponge material, and the thickness layer 312 may be made of the slow-rebound sponge material or partially of the slow-rebound sponge material. A thickness of the pre-connecting layer 311 is in a range of 0.5 mm-3 mm, such as 1 mm. The thinner pre-connecting layer 311 is firstly adhesively bonded to the outer sheet 12, and is then connected to the thickness layer 312. In this way, the outer sheet 12 is more resistant against folding and can maintain the shape better. The support portion 32 is bonded to the thickness layer 312 by a hot melt adhesive, the first flexible rebound layer 2 is further connected to the thickness layer 312, and the thickness layer 312 is disposed between the support portion 32 and the pre-connecting layer 311.

Regarding the material for the thickness layer 312, in the present embodiment, the thickness layer 312 includes a second flexible rebound layer 3121 and a flexible filling layer 3122. The second flexible rebound layer 3121 has the slow-rebound property. The second flexible rebound layer 3121 is connected to the first flexible rebound layer 2 via hot-pressing, and the support portion 32 is disposed between the second flexible rebound layer 3121 and the first flexible rebound layer 2, such that the annular support portion 32 is entirely encapsulated. The material of the second flexible rebound layer 3121 is the same as that of the first flexible rebound layer 2, both are made of the slow-rebound sponge. That is, the second flexible rebound layer 3121 has a second rebound speed. The first flexible rebound layer 2 and the second flexible rebound layer 3121 are made of the same material, and therefore, the first rebound speed of the first flexible rebound layer 2 is the same as the second rebound speed of the second flexible rebound layer 3121. The flexible filling layer 3122 is connected to the second flexible rebound layer 3121 and the pre-connecting layer 311 and is disposed between the second flexible rebound layer 3121 and the pre-connecting layer 311. The flexible filling layer 3122 is made of the conventional sponge material, having a rebound speed faster than the second flexible rebound layer 3121. A thickness of the second flexible rebound layer 3121 is in a range of 1 mm-5 mm, such as 2 mm. A thickness of the flexible filling layer 3122 is in a range of 1 mm-10 mm, such as 8 mm. The second flexible rebound layer 3121 is configured to enhance softness of the thickness layer 312, improving overall softness and comfortable performance of the eye mask. The flexible filling layer 3122 has more sufficient elasticity and is substantially configured to support the eye mask and maintain the overall shape of the eye mask.

For eye masks with different thickness and different extends of softness, desired effects can be achieved by adjusting the thickness of the flexible filling layer 3122 and the thickness of the second flexible rebound layer 3121.

Specifically, the inner sheet 11 is adhesively bonded to the first flexible rebound layer 2, and the pre-connecting layer 311 is also adhesively bonded to the outer sheet 12. The first flexible rebound layer 2, the support portion 32, and the second flexible rebound layer 3121 are connected together via hot-pressing to enable the slow-rebound sponge to completely encapsulate the annular support portion 32 and to maintain the shape of the support portion 32, preventing the support portion 32 from being positionally shifted during using the eye mask. The second flexible rebound layer 3121 is bonded to the flexible filling layer 3122 by the hot melt adhesive, and the pre-connecting layer 311 is bonded to the flexible filling layer 3122 by the hot-melt adhesive. In this way, the thickness design and production of eye masks are facilitated.

Figure 1:
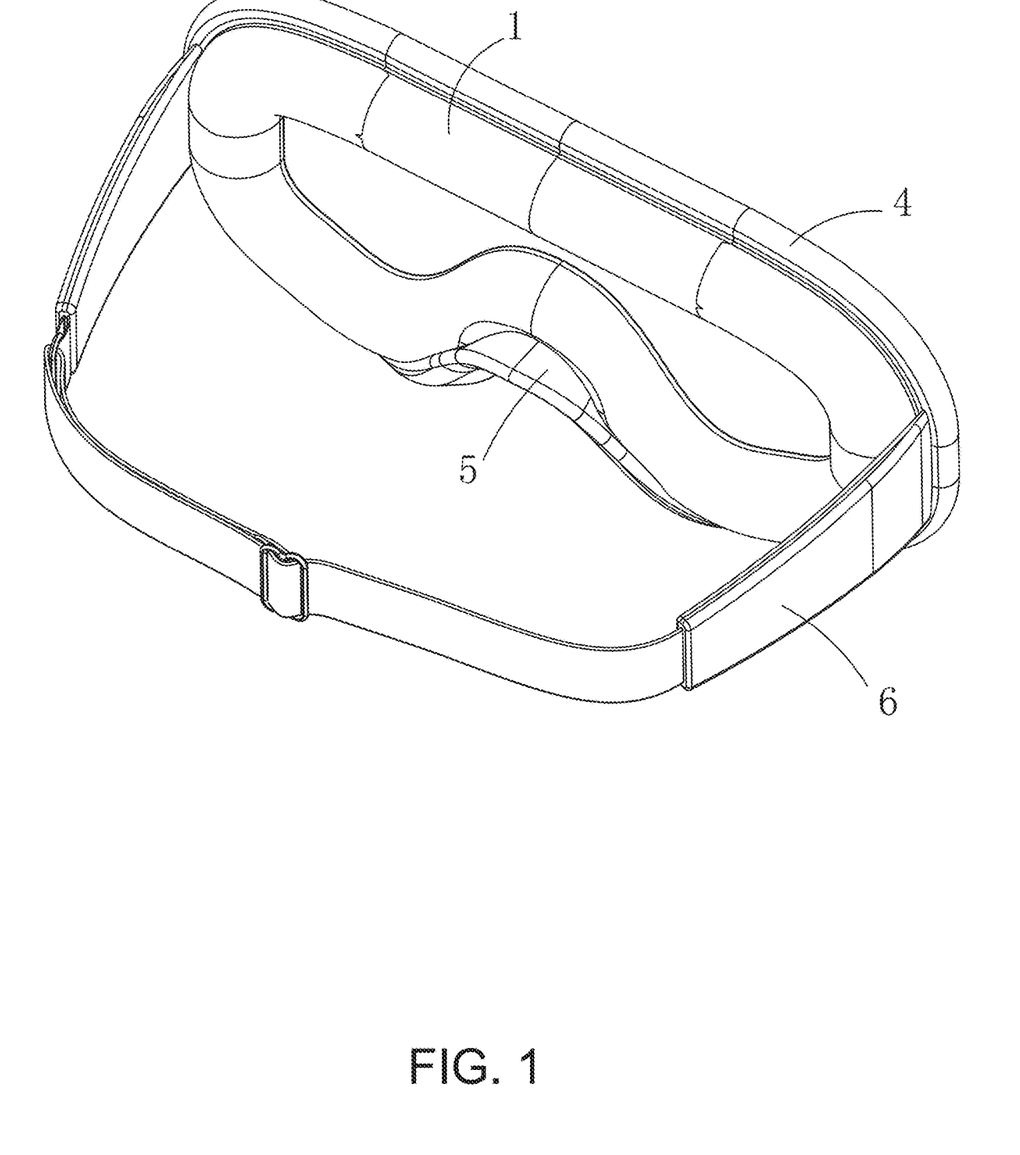
FIG. 1 is a schematic view of an overall structure of the eye mask according to the Embodiment I of the present disclosure.

Furthermore, as shown in FIGS. 1-3, the eye mask further includes a flexible nose support 5. The flexible nose support 5 is sewn to connect to the bottom of the first wrapping layer 1 and located beneath the support portion 32. Specifically, the flexible nose support 5 includes a second wrapping layer 51 and a third flexible rebound layer 52. The second wrapping layer 51 is sewn to connect to the bottom of the first wrapping layer 1 and defines a second accommodating cavity 5101. The third flexible rebound layer 52 has the slow-rebound property, having a third rebound speed. The third flexible rebound layer 52 is arranged in the second accommodating cavity 5101 and is located beneath the support portion 32. A length of the third flexible rebound layer 52 extends along the support portion 32.

In particular, the third flexible rebound layer 52 is made of slow-rebound sponge, which has a weaker elasticity and provides a comfortable pressing sensation. The third flexible rebound layer 52 is substantially configured to reduce the pressure applied by the eye mask on the nose bridge of the user. The length of the third flexible rebound layer 52 is extending along the support portion 32, such that a contact area between the flexible nose support 5 and the face of the user is increased, such that the pressure applied by the eye mask on the face of the user is reduced.

Figure 5:
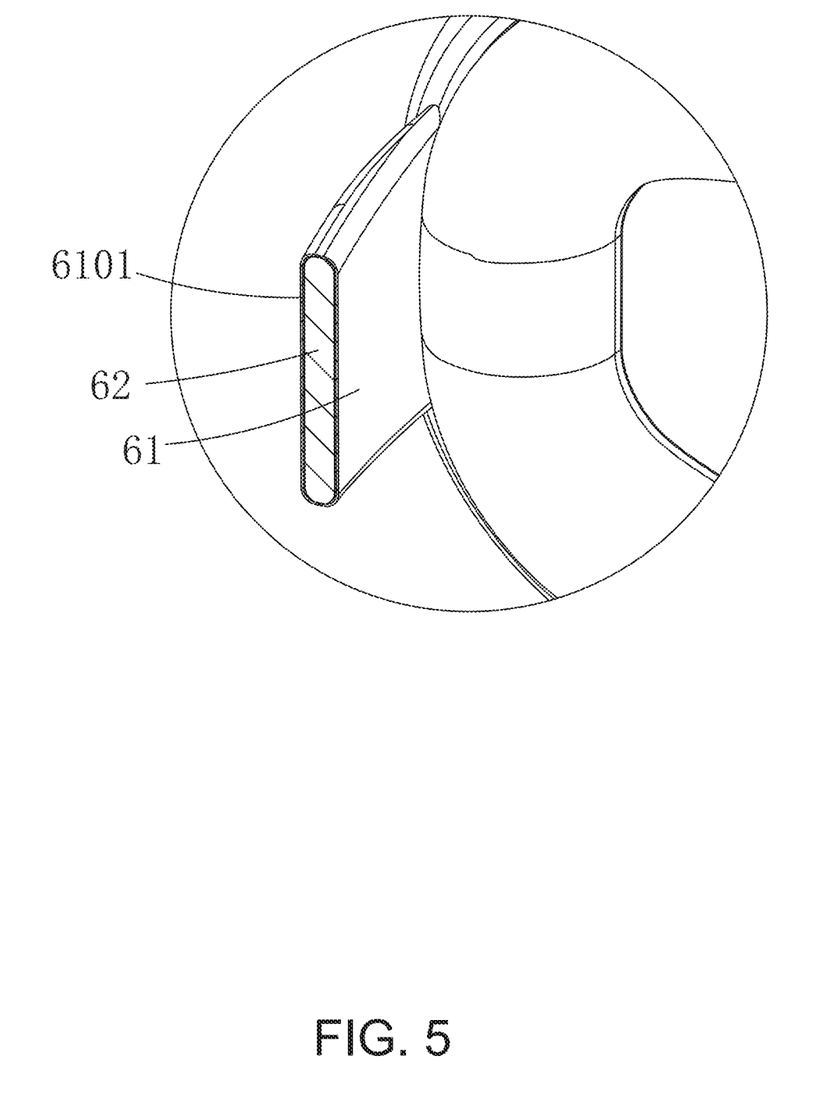
FIG. 5 is a sectional view of a strap according to the Embodiment I of the present disclosure.

In addition, with reference to FIGS. 1 and 5, the eye mask includes a strap 6. The strap 6 is sewn to connect to the first wrapping layer 1, enabling the user to secure the eye mask to the head. Specifically, the strap 6 includes a third wrapping layer 61 and a flexible connecting layer 62. The third wrapping layer 61 is sewn to connect to a side of the first wrapping layer 1 and defines a third accommodating cavity 6101. The flexible connecting layer 62 is received in the third accommodating cavity 6101. The flexible connecting layer 62 is made of the conventional sponge, and therefore, the flexible connecting layer 62 is softer.

The first flexible rebound layer 2, the second flexible rebound layer 3121, and the third flexible rebound layer 52 are all made of slow-rebound sponge (memory sponge), with density ranges all above 45D (D=kg/m$^3$). The aforementioned support portion 32, the flexible filling layer 3122, and the pre-connection layer 311 are all made of the conventional sponge, with density ranges all between 25D and 35D (D=kg/m$^3$). A rebound time of the slow-rebound sponge is typically between 1 s and 3 s, whereas the conventional sponge recovers instantaneously with no delay.

The density of the sponge can be calculated through the following steps.

Step 1: a mass of the sponge is measured.

Step 2: a volume of an irregular sponge is determined by means of a sand replacement method.

Step 3: the density of the sponge is calculated by means of the density formula $p=m/V$.

In regard to manufacture of the eye mask, to facilitate production and processing, following steps are performed.

Step 1, the first flexible rebound layer 2 and the pre-connecting layer 311 are shaped.

Step 2, the inner sheet 11 and the first flexible rebound layer 2 are adhesively bonded together, and the outer sheet 12 and the pre-connecting layer 311 are adhesively bonded together.

Step 3, the support portion 32, the second flexible rebound layer 3121, and the flexible filling layer 3122 are respectively shaped.

Step 4, the first flexible rebound layer 2 and the second flexible rebound layer 3121 are bonded together by hot-pressing, and the support portion 32 is wrapped between the first flexible rebound layer 2 and the second flexible rebound layer 3121.

Step 5, the second flexible rebound layer 3121 is bonded to one side of the flexible filling layer 3122 by hot-melt adhesive, the pre-connecting layer 311 is bonded to the other side of the flexible filling layer 3122 by hot-melt adhesive, and the bonded product is die-cut at edges to complete the shaping.

Step 6, the third flexible rebound layer 52 is wrapped by the second wrapping layer 51.

Step 7, the flexible connecting layer 62 is wrapped by the third wrapping layer 61.

Step 8, the inner sheet 11, the outer sheet 12, the second wrapping layer 51, and the third wrapping layer 61 are connected together by the hemming member 4.

Figure 6:
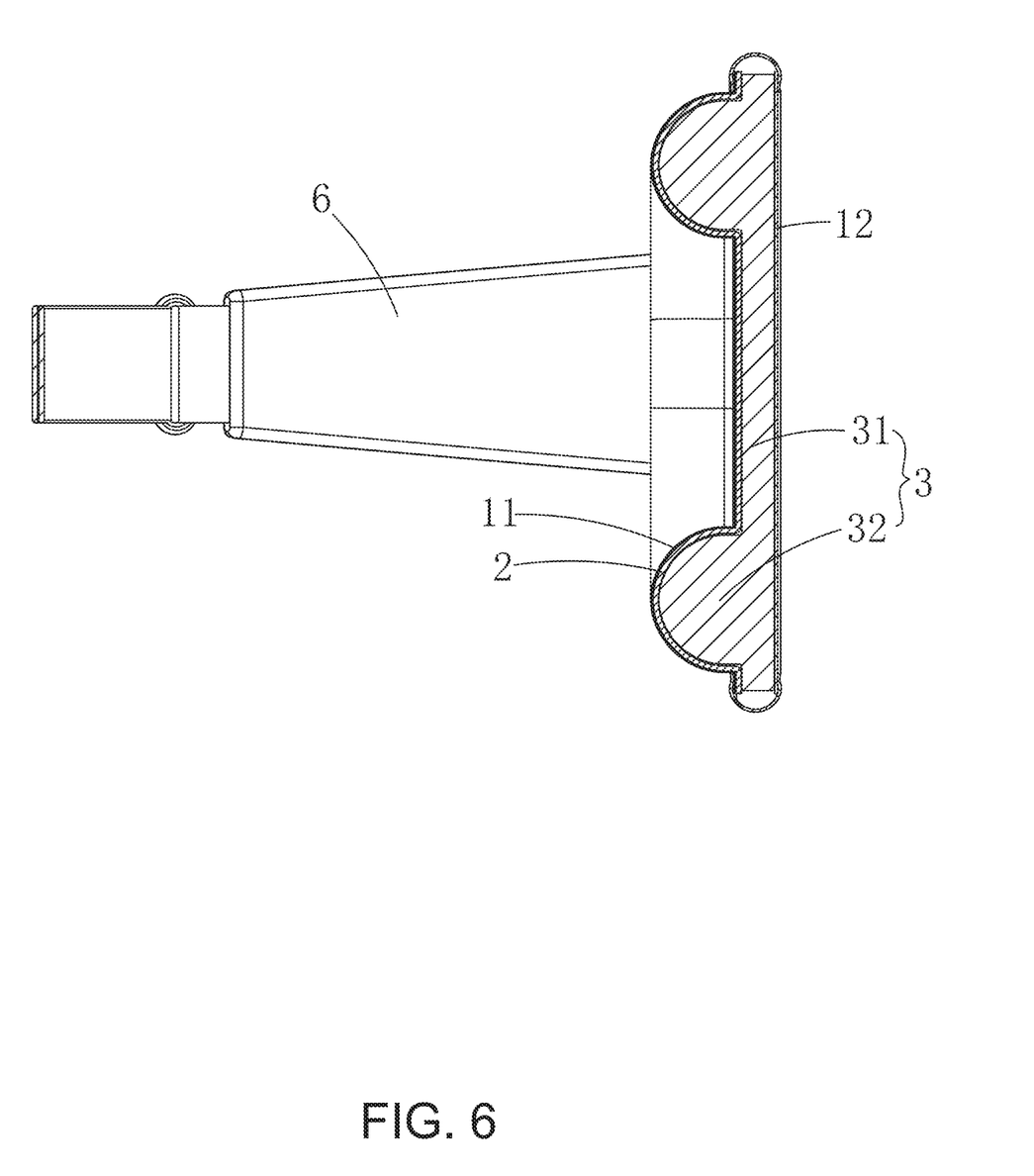
FIG. 6 is a sectional view of the eye mask according to an Embodiment II of the present disclosure.
Figure 7:
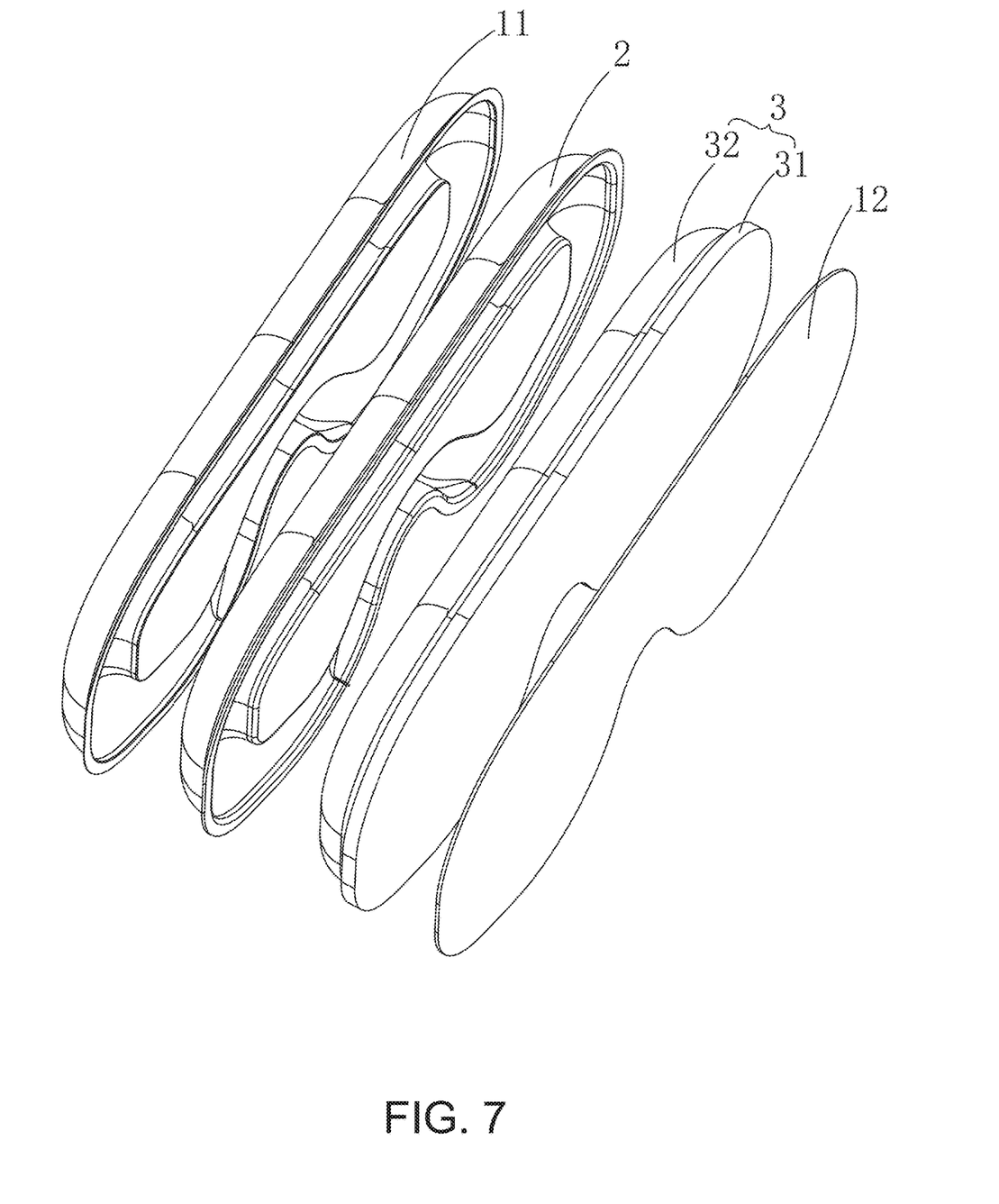
FIG. 7 is an exploded view of a partial structure of the eye mask of the Embodiment II.

With reference to FIGS. 6 and 7, in the embodiment II, the shape-retaining portion 31 and the support portion 32 are integrally formed as a one-piece structure. The shape-retaining portion 31 and the support portion 32 have a same rebound property and both recover faster than the first flexible rebound layer 2. Each of the shape-retaining portion 31 and the support portion 32 is made of the conventional sponge. In the embodiment II, the outer sheet 12 is directly adhesively bonded to the shape-retaining portion 31. The flexible nose support 5 and the strap 6 are also arranged in the embodiment II.

Figure 8:
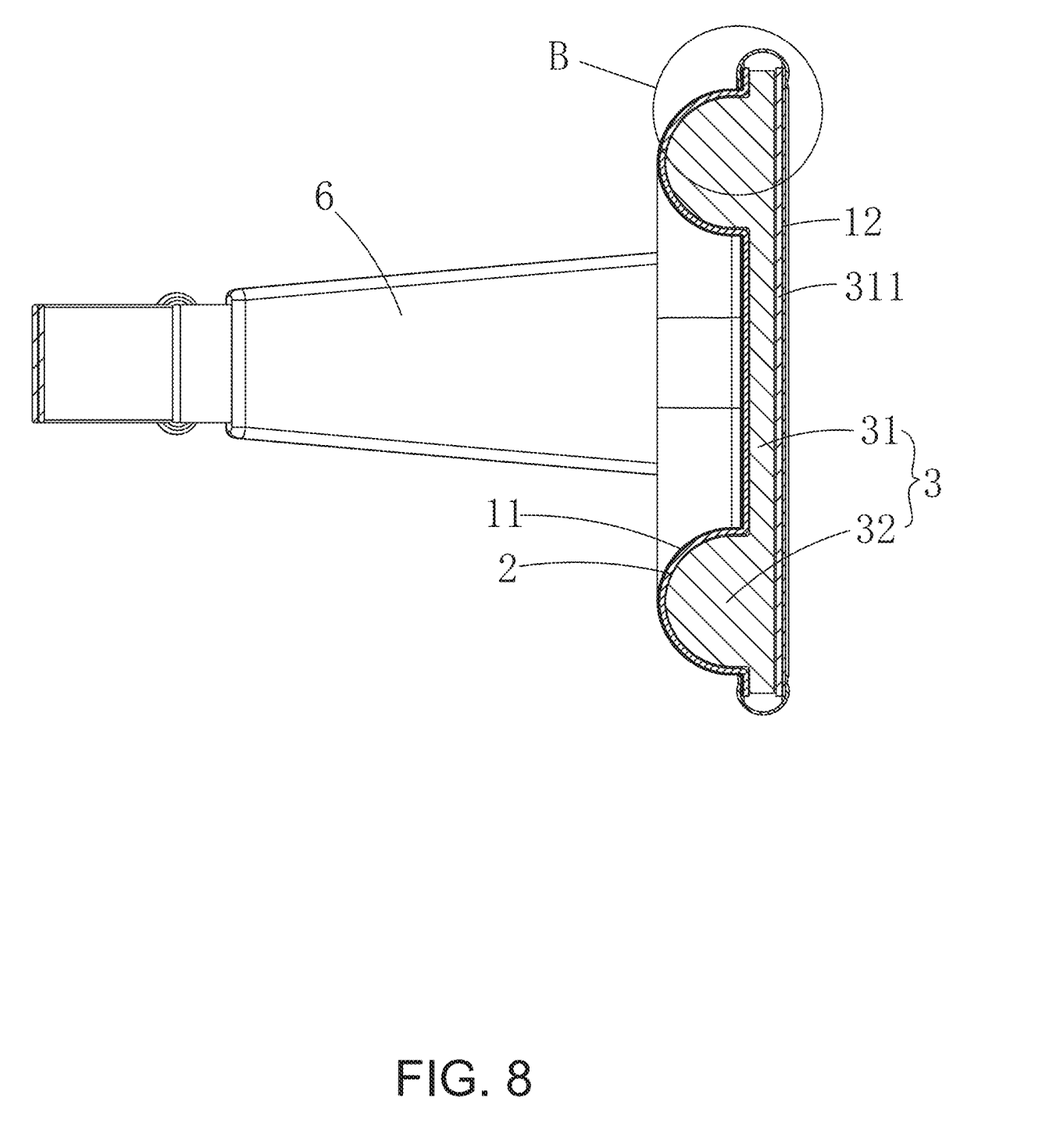
FIG. 8 is a sectional view of the eye mask according to an Embodiment III of the present disclosure.
Figure 9:
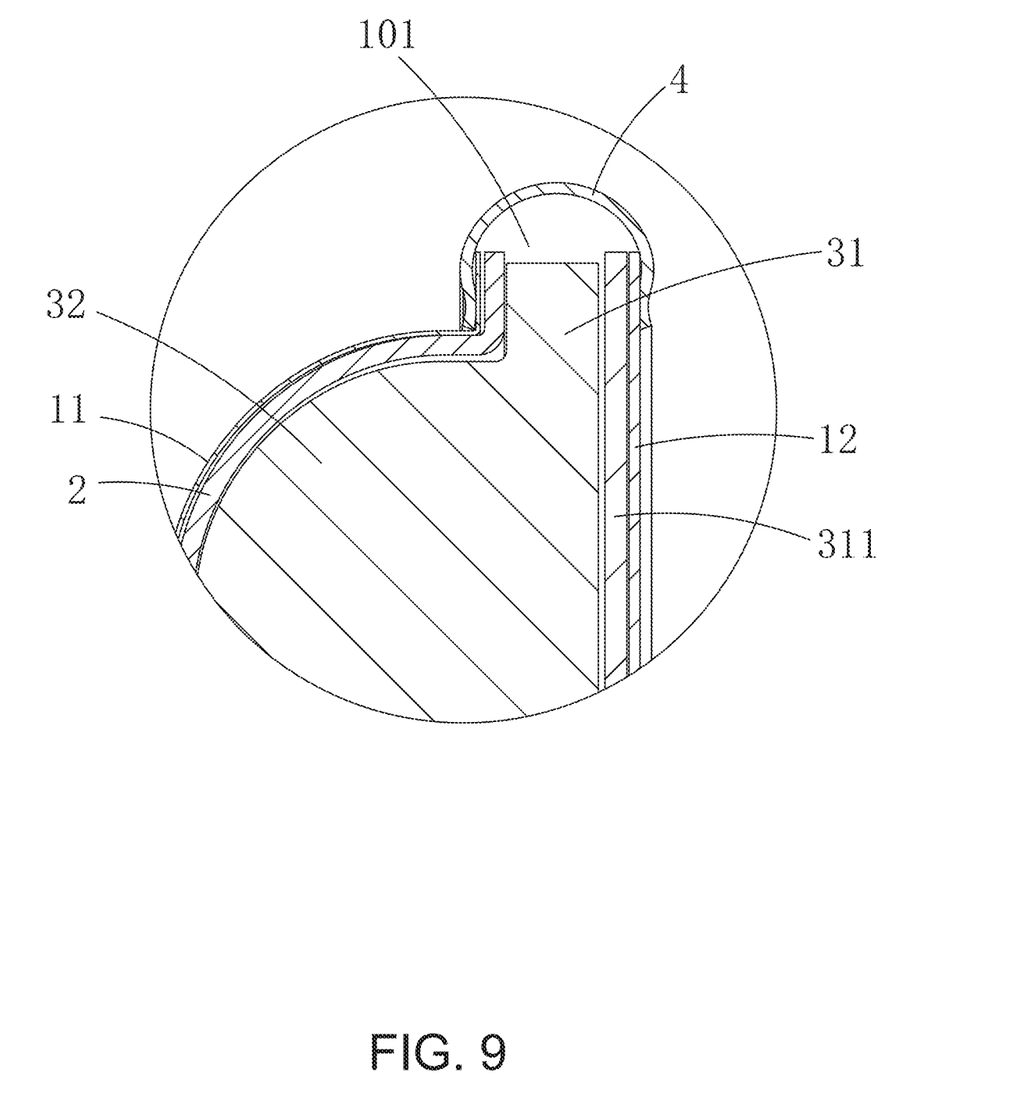
FIG. 9 is an enlarged view of a portion B in FIG. 8.
Figure 10:
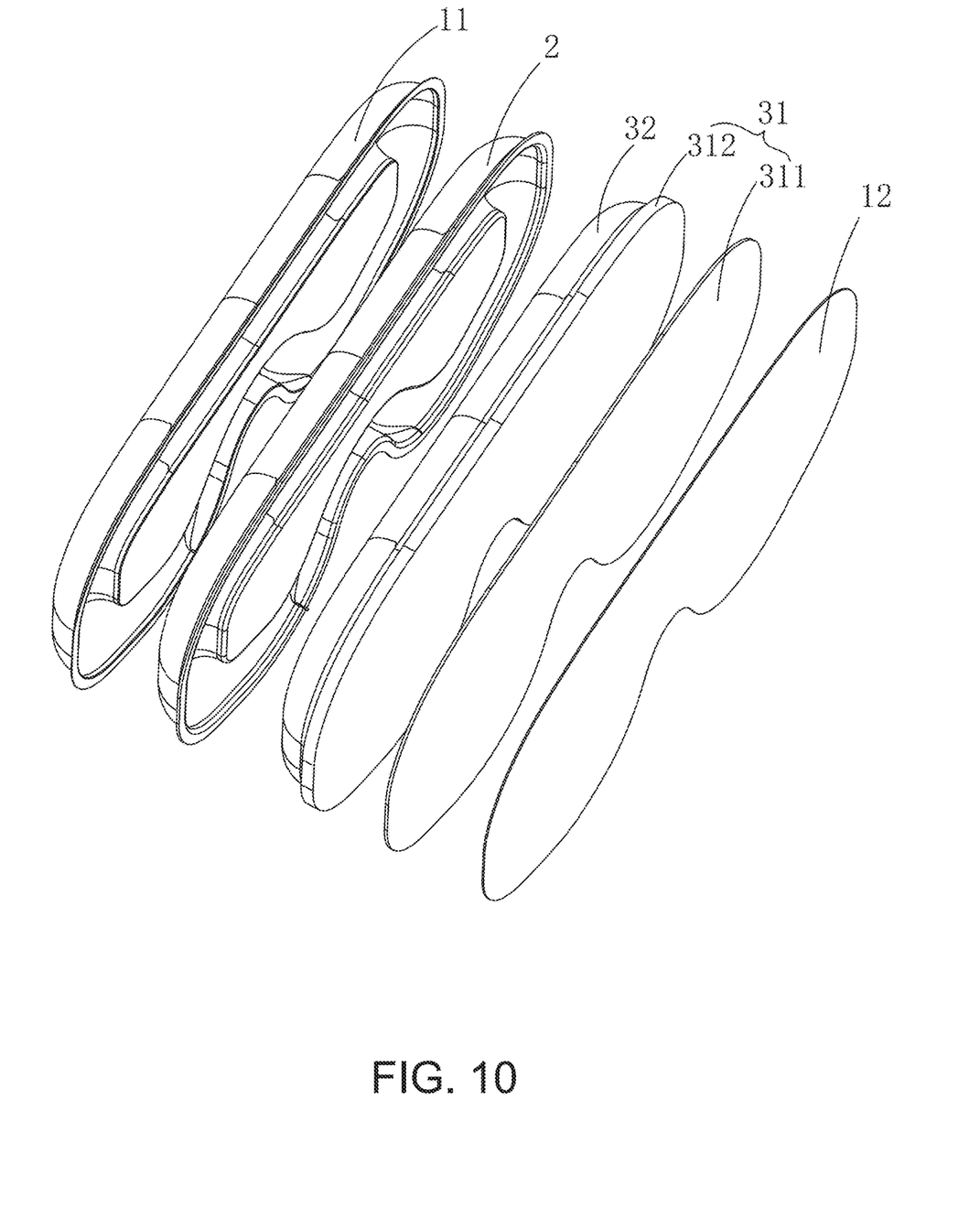
FIG. 10 is an exploded view of a partial structure of the eye mask in the Embodiment III.

Referring to FIGS. 8-10, in an embodiment III, in order to enable the outer sheet 12 to have improved resistance against folding and to have better shape retention, the shape-retaining portion 31 includes the pre-connecting layer 311 and the thickness layer 312. The first flexible rebound layer 2 is connected to the thickness layer 312. The thickness layer 312 and the support portion 32 are integrally formed as a one-piece structure and are both made of the conventional sponge. In the present embodiment, the pre-connecting layer 311 is made of the conventional sponge. By enabling the thinner pre-connecting layer 311 to be firstly adhesively bonded to the outer sheet 12, and subsequently enabling the pre-connecting layer 311 to connect to the thickness layer 312, the outer sheet 12 has the improved resistance against folding and has better shape retention. The flexible nose support 5 and the strap 6 are also arranged in the embodiment III.

Obviously, the embodiments described above are only a part of the embodiments of the present disclosure, and not all of them. The accompanying drawings give some embodiments of the present disclosure, but do not limit the patentable scope of the disclosure, which may be realized in many different forms. Rather, these embodiments are provided for the purpose of providing a more thorough and comprehensive understanding of the present disclosure. Although the present disclosure has been described in detail with reference to the foregoing embodiments, it is still possible for a person skilled in the art to modify the technical solutions recorded in the foregoing specific embodiments or to make equivalent substitutions for some of the technical features therein. Any equivalent structure made by utilizing the contents of the specification and the accompanying drawings of the present disclosure, directly or indirectly applied in other related technical fields, are all the same within the scope of the patent protection of the present disclosure.

What is claimed is:

1. An eye mask, comprising:
   a first wrapping layer, comprising an inner sheet and an outer sheet, wherein a first accommodating cavity is defined between the inner sheet and the outer sheet;
   a first flexible rebound layer, having a slow-rebound property, wherein the first flexible rebound layer has a first rebound speed, and the first flexible rebound layer is received in the first accommodating cavity and attached to the inner sheet; and
   a flexible support layer, received in the first accommodating cavity, attached to the first flexible rebound layer, and connected to the outer sheet, wherein a rebound speed of the flexible support layer is faster than the first rebound speed of the first flexible rebound layer;
   wherein the flexible support layer comprises:
   a shape-retaining portion, having a connecting side facing the inner sheet; and
   a support portion, arranged on the connecting side, wherein the first flexible rebound layer is attached to the connecting side and covers the support portion;
   wherein a rebound speed of the support portion is faster than the first rebound speed of the first flexible rebound layer, and a rebound speed of at least a portion of the shape-retaining portion is slower than the rebound speed of the support portion.

2. The eye mask as claimed in claim 1, wherein the support portion is arranged in a strip shape or a ring shape.

3. The eye mask as claimed in claim 2, wherein the support portion is in a shape of a ring, and is arranged as a closed loop surrounding an edge of the shape-retaining portion.

4. The eye mask as claimed in claim 2, further comprising a flexible nose support, wherein the flexible nose support is sewn to connect to a bottom of the first wrapping layer and is located beneath the support portion.

5. The eye mask as claimed in claim 4, wherein the flexible nose support comprises:
   a second wrapping layer, sewn to connect to the bottom of the first wrapping layer, wherein a second accommodating cavity is defined in the second wrapping layer; and
   a third flexible rebound layer, having the slow-rebound property, wherein the third flexible rebound layer has a third rebound speed and is arranged in the second accommodating cavity and located beneath the support portion, wherein a length of the third flexible rebound layer extends along the support portion, wherein the third rebound speed is substantially the same as the first rebound speed of the first flexible rebound layer.

6. The eye mask as claimed in claim 1, wherein the shape-retaining portion comprises a pre-connecting layer and a thickness layer, the pre-connecting layer is connected to the outer sheet, the support portion is arranged on the thickness layer, the first flexible rebound layer is connected to the thickness layer, and the thickness layer is disposed between the support portion and the pre-connecting layer.

7. The eye mask as claimed in claim 6, wherein the thickness layer comprises:
   a second flexible rebound layer, connected to the first flexible rebound layer and having a slow-rebound property, wherein the second flexible rebound layer has a second rebound speed, the support portion is disposed between the second flexible rebound layer and the first flexible rebound layer; and
   a flexible filling layer, connected to the second flexible rebound layer and the pre-connecting layer and disposed between the second flexible rebound layer and the pre-connecting layer, wherein a rebound speed of the flexible filling layer is faster than the second rebound speed of the second flexible rebound layer.

8. The eye mask as claimed in claim 7, wherein a thickness of the support portion is in a range of 6 mm-15 mm.

9. The eye mask as claimed in claim 7, wherein a thickness of the second flexible rebound layer is in a range of 1 mm-5 mm.

10. The eye mask as claimed in claim 7, wherein a thickness of the flexible filling layer is in a range of 1 mm-10 mm.

11. The eye mask as claimed in claim 7, wherein the inner sheet is adhesively bonded to the first flexible rebound layer, and the pre-connecting layer is adhesively bonded to the outer sheet.

12. The eye mask as claimed in claim 7, wherein the first flexible rebound layer, the support portion, and the second flexible rebound layer are connected together via hot-pressing;
   the second flexible rebound layer is bonded to the flexible filling layer by a hot melt adhesive, and the pre-connecting layer is bonded to the flexible filling layer by a hot-melt adhesive.

13. The eye mask as claimed in claim 7, further comprising a hemming member, wherein the hemming member is arranged along an edge of the first wrapping layer and is sewn to connect the inner sheet to the outer sheet.

14. The eye mask as claimed in claim 7, wherein each of the first flexible rebound layer and the second flexible rebound layer is made of a slow-rebound sponge.

15. The eye mask as claimed in claim 1, wherein a thickness of the first flexible rebound layer is in a range of 0.5 mm-3 mm; and/or
   the first flexible rebound layer is made of a memory sponge, with a density greater than 45 kg/m$^3$.

16. The eye mask as claimed in claim 1, wherein each of the inner sheet and the outer sheet is made of a fabric material.

17. The eye mask as claimed in claim 1, further comprising a strap sewn to connect to the first wrapping layer.

18. The eye mask as claimed in claim 17, wherein the strap comprises:
   a third wrapping layer, sewn to connect to a side of the first wrapping layer, wherein a third accommodating cavity is defined in the third wrapping layer; and
   a flexible connecting layer, received in the third accommodating cavity.

* * * * *